United States Patent
Anagli et al.

(10) Patent No.: US 8,642,558 B2
(45) Date of Patent: Feb. 4, 2014

(54) METHODS, SYSTEMS, AND COMPOSITIONS FOR CALPAIN INHABITION

(75) Inventors: John Anagli, Walled Lake, MI (US); Donald Seyfried, Plymouth, MI (US)

(73) Assignee: Henry Ford Health Systems, Detroit, MI (US)

( * ) Notice: Subject to any disclaimer, the term of this patent is extended or adjusted under 35 U.S.C. 154(b) by 0 days.

(21) Appl. No.: 13/119,675

(22) PCT Filed: Sep. 21, 2009

(86) PCT No.: PCT/US2009/057680
§ 371 (c)(1), (2), (4) Date: May 18, 2011

(87) PCT Pub. No.: WO2010/033912
PCT Pub. Date: Mar. 25, 2010

(65) Prior Publication Data
US 2012/0028904 A1  Feb. 2, 2012

Related U.S. Application Data

(60) Provisional application No. 61/098,592, filed on Sep. 19, 2008.

(51) Int. Cl.
*A61K 36/16* (2006.01)
*C07K 7/02* (2006.01)

(52) U.S. Cl.
USPC .......... 514/21.3; 514/1.1; 514/17.7; 530/317; 530/324

(58) Field of Classification Search
None
See application file for complete search history.

(56) References Cited

U.S. PATENT DOCUMENTS

2002/0042376 A1   4/2002   Karanewsky et al.

FOREIGN PATENT DOCUMENTS

| WO | WO 2007007162 | 1/2007 |
| WO | WO 2012021788 | 2/2012 |
| WO | WO 2012021800 | 2/2012 |
| WO | WO 2010033912 | 3/2012 |

OTHER PUBLICATIONS

Guttmann et al., Identification of a novel calpain inhibitor using phage display, Aug. 12, 2005, BBRC 333(4):1087-1092.*
McCollum et al., Inhibition of calpain-mediated cell death by a novel peptide inhibitor, Dec. 2006, Experimental Neurology 202(2):506-513.*
Linton, S.D. et al., "Oxamyl dipeptide caspase inhibitors developed for the treatment of stroke", Bioorganic & Medicinal Chemistry Letter, 2004, pp. 2684-2691, vol. 14, No. 10.
Lescop, C. et al., "Novel cell-penetrating alpha-keto-amide calpain inhibitors as potential treatment for muscular dystrophy", Bioorganic & Medicinal Chemistry Letters, 2004, pp. 5176-5185, vol. 15, No. 23.

* cited by examiner

*Primary Examiner* — John Ulm
(74) *Attorney, Agent, or Firm* — Blue Filament Law PLLC; Avery N. Goldstein; Marc S. Balban

(57) ABSTRACT

Methods, systems and compositions comprising novel peptidomimetics are disclosed that can be used to inhibit calpain and, more specifically, to treat tissue damage caused by pathologic activation of calpains.

13 Claims, 6 Drawing Sheets

METHODS, SYSTEMS, AND COMPOSITIONS FOR CALPAIN INHABITION

BACKGROUND

Stroke by blockage of cerebral artery supplying blood to the brain is a major cause of death and disability worldwide. Stroke in mammals, including in humans, often presents clinically as a disruption of blood flow to the brain and other parts of the neurological system. Mechanistically, this disruption of blood flow often results in ischemia, which can produce damage, death, and/or other injury to the tissue or organ with comprised blood flow. The etiology of ischemic injury is sometimes mediated at the molecular level.

Despite its public heath significance, treatment of ischemic stroke is limited to thrombolysis by tissue plasminogen activator administered intravenously within three hours of symptom onset. Only a small percentage (<5%) of stroke patients ultimately receive this treatment.

Calpain is a cysteine protease located in the cytosol of all cells, including neurons, and is implicated in cell death as part of the calcium modulated cascade of enzymatic events after ischemic damage. Dysregulation of calpain, a prominent cysteine proteinase recognized to play an important role in signal transduction, cell migration and regulation of apoptosis, has been implicated in a variety of neurodegenerative disorders, including tissue damage, following stroke, traumatic brain and spine injury. It has also been linked to pathogenesis of a variety of neurological diseases, such as multiple sclerosis, and Alzheimer's, Huntington's and Parkinson's disease. These disorders are characterized by intracellular calcium overload leading to excessive activation of calpains. In vivo inhibition of calpain using cysteine protease inhibitors (e.g. peptide aldehydes, alpha-keto esters and amides) diminishes the extent of neuronal damage following ischemia; however, none of these inhibitors is specific for calpain, since they also effectively inhibit other cysteine proteases as well.

Treatments for neurodegenerative diseases and brain pathologies remain limited. Previous calpain inhibitors have been studied as a potential treatment strategy for stroke, but these inhibitors are not selective for calpain and may incur unwanted side effects by their interaction with other proteases. Thus, an unmet need remains for methods, systems, and compositions for selectively inhibition of calpain and without unwanted side effects.

BRIEF SUMMARY

Without limitation to only those embodiments expressly disclosed herein and without disclaiming any embodiments, some embodiments of the invention comprise methods, systems, and compositions to selectively inhibit biologically active calpain. In some embodiments, such inhibition may be used to treat cell, tissue, or organ damage in a patient by administering to said patient a therapeutically effective amount of a peptidomimetic specific for calpain.

BRIEF DESCRIPTION OF THE DRAWINGS

Some embodiments of the present invention will now be described, by way of example only and without disclaimer of other embodiments, with reference to the accompanying drawings (in which "B27-HYD" refers to SEQ ID NO: 5, as discussed herein):

DETAILED DESCRIPTION

Figure 1:
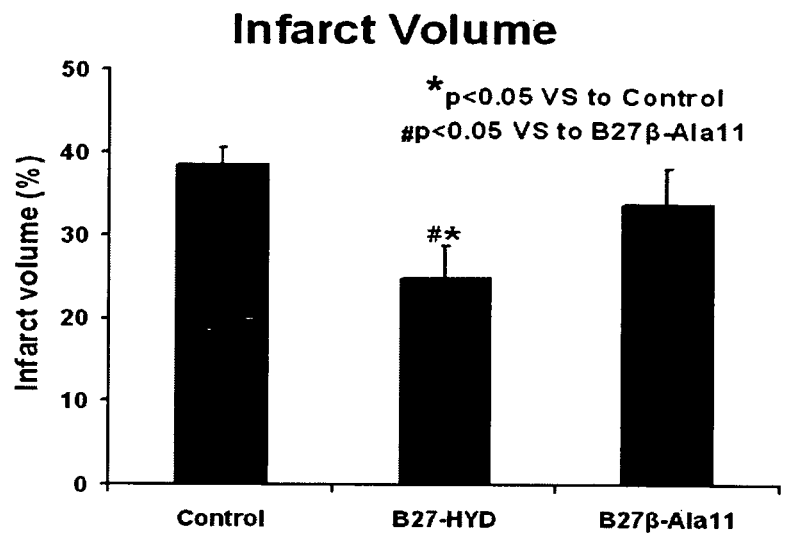
FIG. 1 is a chart showing infarct volume in treated and control subjects.

Without limitation to only those embodiments expressly disclosed herein and without disclaiming any embodiments, some embodiments of the invention comprise methods, systems, and compositions to selectively inhibit biologically active calpain. In some embodiments, such inhibition may be used to treat cell, tissue, or organ damage in a patient by administering to said patient a therapeutically effective amount of a peptidomimetic specific for calpain.

We have discovered, isolated, and/or made novel structures for selective calpain inhibitors which, among other uses, can reduce the effects of cerebral ischemia in mammals, including without limitation, human beings. Without limitation, some embodiments of the present invention are directed to methods, systems, and/or compositions for reducing tissue damage in a mammal resulting from excessive activation of calpain. Such compositions useful for this purpose comprise calpastatin-based peptidomimetics which are specific inhibitors of calpain.

Some embodiments comprise peptidomimetic versions of compounds that contain a number of non-peptidic chemical bonds, non-proteinogenic amino acids, and/or conformational constraints.

We have isolated, synthesized and/or modified a nucleotide as well as related amino acid sequence of the native 27-amino acid calpastatin-derived peptide to develop peptidomimetic calpain inhibitors of some embodiments, as follows:

```
                                              (SEQ ID NO: 1)
acc caa tgg cta cta cct acc taa gag gaa ttg ggt aaa aga gaa gtc aca att cct cca aaa tat agg gaa cta ttg gct
                                              (SEQ ID NO: 2)
Asp Pro Met Ser Ser Thr Tyr Ile Glu Glu Leu Gly Lys Arg Glu Val Thr Ile Pro Pro Lys Tyr Arg Glu Leu Leu Ala
```

In some embodiments, side-chain to side-chain cyclization is performed between $Lys^{21}$ and $Glu^{24}$ side chains of SEQ ID No. 2.

Some embodiments comprise the following natural amino acid replacements in SEQ ID NO: 2:
$Arg^{23}$ to $Val^{23}$
$Glu^{24}$ to $Ala^{24}$
$Ala^{27}$ to $Pro^{27}$, thus providing a sequence Asp Pro Met Ser Ser Thr Tyr Ile Glu Glu Leu Gly Lys Arg Glu Val Thr Ile Pro Pro Lys Tyr Val Ala Leu Leu Pro (SEQ ID NO: 3). In some embodiments, the hydrophobic sequence Ala Val Leu Leu Ala Leu Leu Ala Pro (SEQ ID NO: 4) is added to the C-terminus of SEQ ID NO: 3 to provide a sequence of Asp Pro Met Ser Ser Thr Tyr Ile Glu Glu Leu Gly Lys Arg Glu Val Thr Ile Pro Pro Lys Tyr Val Ala Leu Leu Pro Ala Val Leu Leu Ala Leu Leu Ala Pro (SEQ ID No: 5).

In some embodiments, one or more of the more usual peptidic bonds between the following amino acid pairs of SEQ ID NO: 2, SEQ ID NO: 3, or SEQ ID NO. 5 are replaced with non-peptidic reduced amide bonds rendering the peptidomimetic resistant to cleavage by proteolytic enzymes in vivo, and consequently improving its pharmacokinetic properties:
$Ser^4$-$Ser^5$
$Tyr^6$-$Ile^7$
$Lys^{13}$-$Arg^{14}$
$Glu^{15}$-$Val^{16}$
$Lys^{21}$-$Tyr^{22}$
$Tyr^{22}$-$Arg^{23}$
$Arg^{23}$-$Glu^{24}$.

Moreover, in some embodiments, one or more of the following natural to un-natural amino acid substitutions are made in SEQ ID NO: 2, SEQ ID No: 3, or SEQ ID NO: 5:
$Ile^{18}{\rightarrow}Nva^{18}$
$Arg^{23}$-$Orn^{23}$
providing sequences:

```
                                              (SEQ ID NO: 6)
Asp Pro Met Ser Ser Thr Tyr Ile Glu Glu Leu Gly

Lys Arg Glu Val Thr Nva Pro Pro Lys Tyr Orn Glu

Leu Leu Ala,
                                              (SEQ ID NO: 7)
Asp Pro Met Ser Ser Thr Tyr Ile Glu Glu Leu Gly

Lys Arg Glu Val Thr Nva Pro Pro Lys Tyr Arg Glu

Leu Leu Ala,
                                              (SEQ ID NO: 8)
Asp Pro Met Ser Ser Thr Tyr Ile Glu Glu Leu Gly

Lys Arg Glu Val Thr Ile Pro Pro Lys Tyr Orn Glu

Leu Leu Ala;
                                              (SEQ ID NO: 9)
Asp Pro Met Ser Ser Thr Tyr Ile Glu Glu Leu Gly

Lys Arg Glu Val Thr Nva Pro Pro Lys Tyr Val Ala

Leu Leu Pro,
or
                                              (SEQ ID No: 10)
Asp Pro Met Ser Ser Thr Tyr Ile Glu Glu Leu Gly

Lys Arg Glu Val Thr Nva Pro Pro Lys Tyr Val Ala

Leu Leu Pro Ala Val Leu Leu Ala Leu Leu Ala Pro.
```

In some embodiments, without limitation, the compounds contain a hydrophobic blood-brain-barrier ("BBB") or membrane-permeant amino acid sequence linked by a polyethylene glycol linker to the N-terminus of the peptidomimetic inhibitor. Without limitation, one example of a hydrophobic membrane-permeant amino acid sequence, and related nucleotide sequence, comprising embodiments of the invention as follows:

```
                                              (SEQ ID NO: 11)
gcc gcg gta gcg ctg ctc ccg gcg gtc ctg ctg gcc ttg ctg gcg ccc
                                              (SEQ ID NO: 12)
Ala Ala Val Ala Leu Leu Pro Ala Val Leu Leu Ala Leu Leu Ala Pro.
```

Non-peptidic BBB permeant structures such as taurine, cholesterol, a nonionic amphiphilic diethylene glycol methyl moiety, etc. can also be optionally attached to the inhibitor.

Dysregulation of calpain, a cysteine proteinase recognized to play an important role in signal transduction, cell migration and regulation of apoptosis, has been implicated in a variety of neurodegenerative disorders, including tissue damage, following stroke, traumatic brain and spine injury. These disorders are characterized by intracellular calcium overload leading to excessive activation of calpains. In vivo inhibition of calpain using cysteine protease inhibitors (e.g. peptide aldehydes, alpha-keto esters and amides) diminishes the extent of neuronal damage following ischemia; however, the relative nonspecificity of these cysteine proteinase inhibitors precludes a definitive role for calpain participation. Calpastatin is the only inhibitor that is specific for calpain, and it is generally accepted that the interaction of calpastatin with calpain is the most relevant mechanism responsible for the regulation of $Ca^{2+}$-induced proteolysis. The deduced primary structure of calpastatin consists of a non-inhibitory L-domain and four repeating inhibitory domains, each having an independent inhibitory activity against calpain and thus constituting a functional unit (See Emori et al, "All four repeating domains of the endogenous inhibitor for calcium-dependent protease independently retain inhibitory activity. Expression of the cDNA fragments in *Escherichia coli*", *J. Biol. Chem.* 263, 2364-2370).

We previously identified two "hot spots" within the calpastatin molecule in which side chains of the most critical residues of calpastatin interact with hydrophobic pockets in calpain. Mutation of any of the key residues in either hot spot results in loss of inhibitory activity. Our work indicates that different regions in the inhibitory domain of calpastatin interact with complementary sites in calpain and undergo calpain-induced conformational changes that are crucial to inhibitor's affinity and selectivity. Our results indicate that specific inhibition of calpain in vivo by administration of novel membrane-permeant calpastatin peptide(s) reduces infarct volume and neurological deficits by blocking post-ischemic proteolysis of vital brain proteins.

EXAMPLES

The following examples of some embodiments of the invention are provided without limiting the invention to only those embodiments described herein and without disclaiming any embodiments.

Example 1

Dysregulation of calpain, a prominent cysteine protease recognized to play an important role in signal transduction, cell migration, and regulation of apoptosis, has been implicated in tissue damage following ischemic stroke. We have discovered, isolated, and/or made inhibitors of calpain which are specific for calpain.

We developed our peptidomimetic inhibitors of calpain by rational and systematic chemical modifications of the amide bond and/or side chain functionalities of permutations of SEQ ID NO: 2, followed by calpain-inhibitory kinetic measurements of the designed molecules in vitro as well as an assessment of their ability to improve neurological recovery in vivo after focal cerebral ischemia in rats. The structural modifications performed to create the peptidomimetics included, without limitation, amino acid replacements by chemical mutagenesis, amide bond mimics, methylene group insertion between the α-carbon and the carbonyl functionalities of individual amino acids, replacement of natural amino acid side chains with non-natural moieties, and amino acid side chain cyclizations. Calpain-inhibitory activity of the peptidomimetics was measured by steady-state and stopped-flow enzyme inhibition kinetic studies using purified calpain and natural protein or synthetic fluorogenic peptide substrates. The effect of the peptidomimetics on cerebral infarction, cerebral endothelial function and neurological functional recovery after ischemic stroke was assessed using a rat model of 2 hour middle cerebral artery ("MCAO") ischemia.

Based on our studies, we selected and further tested SEQ ID NO: 5 for its cerebroprotective capacity after 2 hour middle cerebral artery ("MCAO") ischemia in the rat. Two hour MCAO by the suture method was induced in 21 male Wistar rats. Following reperfusion, intravenous saline (n=9), SEQ ID NO: 5 (3 mg/kg; n=9), or SEQ ID NO: 5-βAla (3 mg/kg; an inactive form of SEQ ID NO: 5, B27 β-Ala$^{11}$ in figures, n=9) was administered for 4 hours. Animals survived 7 days and neurological testing (score 0-3, 3 being the most severe) was performed. After sacrifice the brain samples were formalin fixed and infarct volumes were calculated using standard computerized image analysis. Independent t-test was used for statistical analysis.

Figure 2:
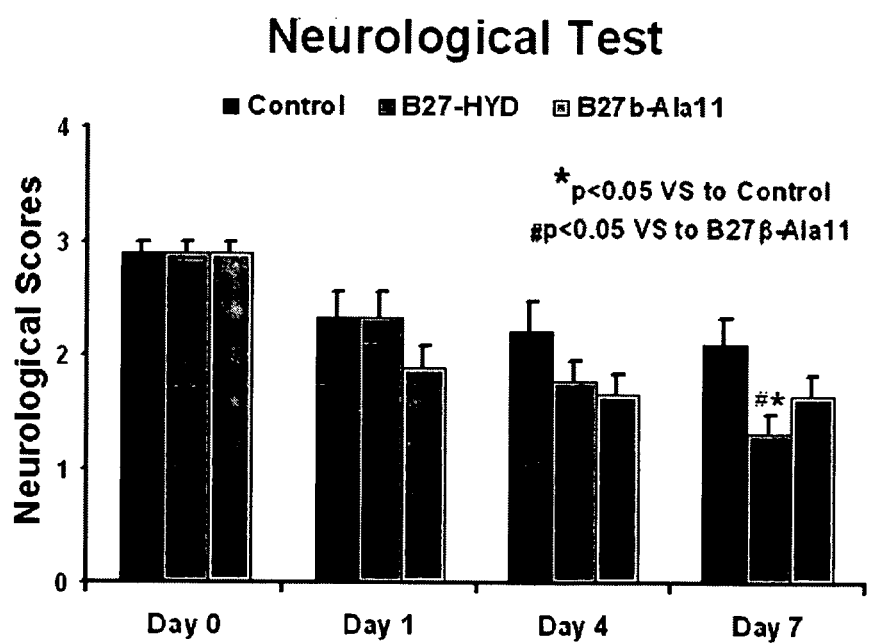
FIG. 2 shows the results of neurological testing in control and treated subjects.

All animals survived 7 days post MCA occlusion and treatment. As shown in FIGS. 1 and 2 (in all Figures herein, "B27-HYD" refers to SEQ ID NO: 5), the group receiving SEQ ID NO: 5 had significantly reduced infarct volume compared to the saline and a less active Leu$^{11}$ to βAla$^{11}$ version of SEQ ID NO: 5, Asp Pro Met Ser Ser Thr Tyr Ile Glu Glu βAla Gly Lys Arg Glu Val Thr Ile Pro Pro Lys Tyr Val Ala Leu Leu Pro Ala Val Leu Leu Ala Leu Leu Ala Pro (SEQ ID NO: 13), SEQ ID NO: 5 with β-Ala$^{11}$ treated rats (24.9±3.8 vs 38.4±2.1 and 33.8±4.2; mean±SEM, p<0.05). As shown in FIG. 2, neurological scores, derived from behavioral and observational tests of control and treated animals, were significantly improved at 7 days in the SEQ ID NO: 5 treated group compared to the saline and SEQ ID NO: 13 (β-Ala$^{11}$ treated) groups (1.00±0.17 vs 1.78±0.22 and 1.44±0.18, mean±SEM, p<0.05).

We discovered that our selective calpain inhibitors are cerebroprotective after transient MCA occlusion in the rat. One advantage of studying the mechanism of cerebral ischemia with SEQ ID NO: 5 is its ability to selectively inhibit calpain, compared to other non-calpastatin derived compounds. Selectively blocking calpain after cerebral ischemia will enable further understanding of calpain's specific role in post-ischemic neuronal damage as well as increasing therapeutic options.

Example 2

Calpastatin, a naturally occurring protein, is the only inhibitor that is specific for calpain, and it is generally accepted that the interaction of calpastatin with calpain is the most relevant mechanism responsible for the regulation of $Ca^{2+}$-inducted proteolysis. We have identified two "hot spots" in the peptide of SEQ ID NO: 2 that contain the residues critical for the potent and specific inhibition of calpain. To the best of our knowledge, none of the studies reported to date on the pharmacologic inhibition of calpain has benefited from the absolute specificity of calpastatin to delineate calpain's contribution to cell death and neurological dysfunction following ischemic stroke. Thus, we evaluated SEQ ID NO: 5, one embodiment of a novel BBB-permeant analogue of SEQ ID NO: 2, for its effect on cerebral infarction and neurological functional recovery after focal cerebral ischemia in rats.

Materials and Methods

Animal Model.

Following an institutionally approved animal care protocol, male Wistar rats (270-290 g) were obtained from Charles River Breeding Co. (Wilmington, Mass., USA). Two-hour middle cerebral artery occlusion (MCAO) by the intravascular suture method, drug infusion, measurement of infarct volume and neurological deficits were performed as detailed previously.

SEQ ID NO: 5 and its less active Leu$^{11}$ to βAla$^{11}$ mutant SEQ ID NO: 13 were prepared by FMOC-chemistry solid phase peptide synthesis and characterized for calpain inhibitory activity. SEQ ID NO: 5 (50 μM solution, i.v. infusion at 15 μl/min for 4 h; 3 mg/kg), SEQ ID NO: 13 or vehicle (1% DMSO in saline) was administered to rats 97 (n=6-9) immediately after reperfusion following 2 h of MCAO. Sham-operated animals had surgery but no MCA occlusion. Animals to be studied for neurological score and infarct volume survived 7 days.

Brain protein extraction and Western blot analysis.

Following MCAO and drug infusion, the animals were sacrificed after 24 or 48 h of survival. At that time, the brains were extracted and separated into right and left, cortical and subcortical regions, snap-frozen in liquid nitrogen and stored at −80° C. until used. For Western blot analysis, the brain samples were pulverized to a fine powder with a small mortar and pestle set over dry ice. The pulverized brain tissue powder was homogenized in a solution of 0.25 M sucrose, 25 mM 2-(N-morpholino)-ethanesulfonic acid, 1 mM EDTA, pH 6.5, containing 0.025 mM E-64, 2.0 mM AEBSF, 0.5 mM PMSF, 0.02 mM leupeptin, 0.05 mM pepstatin, and 0.001 mM aprotinin (homogenization buffer) at 4° C. in a Potter-Elvehjem homogenizer. The homogenates were then centrifuged at 4° C. for 20 min at 16,000 g. Aliquots of the supernatant were stored at −80° C. until used for experiments. Protein concentrations were determined using micro BCA Protein Assay kit (Pierce, Rockford, Ill.). SDS-PAGE was carried out according to Laemmli and immunoblots were performed according to the technique of Towbin et al. Mouse monoclonal anti-all-spectrin antibody (MAB 1622, 1:1,000) and horse radish peroxidase (HRP)-conjugated goat anti-mouse IgG (AP124P, 1:10,000) were from Chemicon (Temecula, Calif.). Labeled proteins were detected with the enhanced chemiluminescence method according to the manufacturer's instructions (GE Healthcare Biosciences, Piscataway, N.J., USA). Bands were quantified by densitometry using Gel-Doc 2000 (Bio-Rad, Richmond, Va.) and the free open source software ImageJ.

Results:

Infarct Volume.

Figure 3:
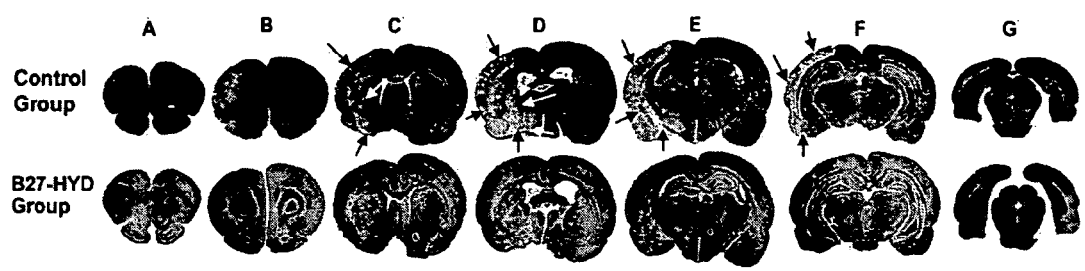
FIG. 3 is a photograph of stained tissue sections for control and treated brain tissue.

From the H&E sections, the ischemic core area with diffuse pallor of the eosinophilic background and the border area with vacuolation or sponginess and neutrophils can be identified under the microscope. As can be seen from the representative H&E stained serial coronal sections A through G in FIG. 3, the brain region mostly affected by the ischemia is the cortex in the MCA distribution (black arrows). The subcortical region in the core slices of C and D is also affected (white arrows). The ischemic damage (i.e. cell death, loss of tissue, or encephalomalacia) is less in the SEQ ID NO: 5-treated animals compared to the vehicle-treated controls. By comparison, the contralateral side appeared undamaged by both gross inspection and in histological sections. As shown in Table 1 and FIG. 1, SEQ ID NO: 5 significantly reduced infarct volume compared to SEQ ID NO: 13-treated (24.9±3.8% vs. 33.8±4.2%, percent hemispheric infarct volume±SE; #P<0.05, independent t-test; n=9 per group) and vehicle-treated (24.9±3.8% vs. 38.4±2.1%, percent hemispheric infarct volume±SE; *P<0.05, independent t-test; n=9 per group) controls, respectively.

TABLE 1

Q1 Summary of data for infarct volume and neurological functional outcome.

| Group | Lesion Volume % of Hemisphere | Neurological Score | | | |
|---|---|---|---|---|---|
| | | 0 Day | 1 Day | 4 Days | 7 Days |
| Saline (n = 9) | 38.4 ± 2.1 | 2.89 ± 0.11 | 2.33 ± 0.24 | 1.89 ± 0.24 | 1.78 ± 0.22 |
| SEQ ID NO: 5 (n = 9) | 24.9 ± 3.8*,# | 2.89 ± 0.11 | 2.33 ± 0.24 | 1.44 ± 0.18 | 1.00 ± 0.17*,# |
| SEQ ID NO: 13 (n = 9) | 33.8 ± 4.2 | 2.89 ± 0.11 | 2.11 ± 0.20 | 1.56 ± 0.18 | 1.44 ± 0.18 |

Values are mean ± SE.
*P < 0.05 SEQ ID NO: 5 vs. vehicle.
P < 0.05 SEQ ID NO: 5 vs. SEQ ID NO. 13

Neurological Score.

Neurological scores have been previously defined as follows: no observable deficit=0, forelimb flexion=1, decreased resistance to lateral push with forelimb flexion=2, same behavior as 2 plus circling=3. The behavioral data indicate that the neurological scores slightly improved in all the experimental groups during the first 4 days post-injury (Table 1 and FIG. 2). However, the difference in performance between the SEQ ID NO: 5-treated animals and the vehicle controls (1.00±0.17 vs. 1.78±0.22, *P<0.05, n=9 per group; independent t-test) and the SEQ ID NO: 13-treated group (1.00±0.17 vs. 1.44±0.18, #P<0.05, n=9 per group; independent t-test) was statistically significant at day 7 post-injury.

αII-Spectrin Breakdown.

Figure 4:
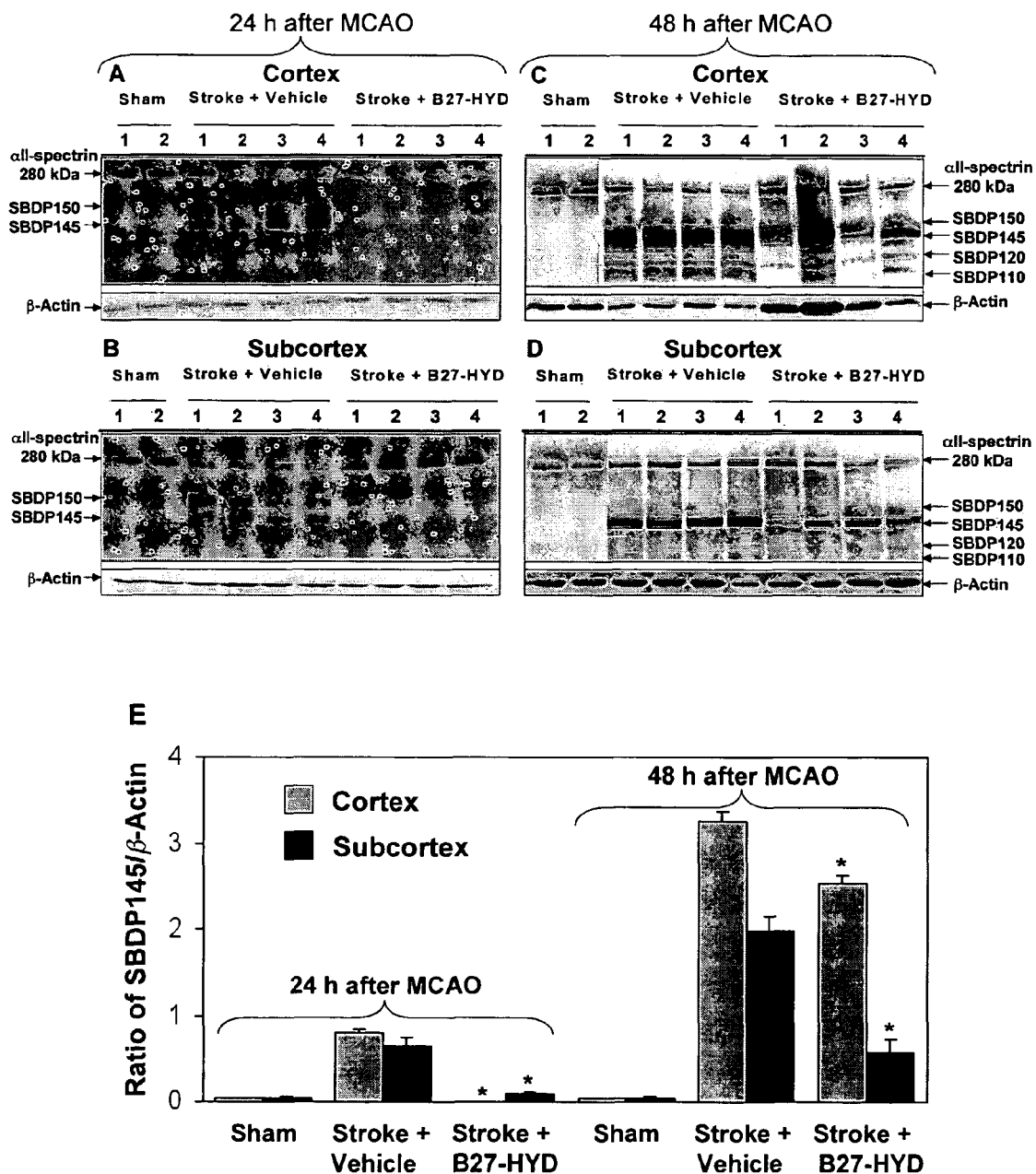
FIG. 4 shows data concerning relative αII-spectrin levels in test and control animals.

Pathologic activity of calpain and in vivo efficacy of SEQ ID NO: 5 were assessed by Western blot analysis of all-spectrin breakdown products (SBDPs) generated in the rat brain following MCAO. FIG. 4 shows data indicating that SEQ ID NO: 5 blocks calpain-mediated cleavage of αII-spectrin in rat brain following MCAO: (A-D) Representative immunoblots of αII-spectrin in ipsilateral cortical (A,C) and subcortical (B,D) regions of sham-operated, ischemic vehicle-treated, and ischemic SEQ ID NO: 5-treated animals at 24 h (A,B) and 48 h (C,D) following MCAO. Intact αII spectrin (280 kDa), SBDP150, SBDP145, SBDP120 and SBDP110 are demonstrated. (E) Densitometric analysis of SBDP150/SBDP145 levels in ipsilateral cortex and subcortex at 24 and 48 h following MCAO.

As can be seen in FIG. 4, brain samples from sham-operated animals present mainly the intact αII-spectrin (280-kDa) while the stroke-injured vehicle-treated animals (vehicle controls) had elevated levels of 150- and 145-kDa SBDPs (SBDP150 and SBDP145) in the cortical and subcortical regions of the ipsilateral hemisphere in the first 24 h post-injury (panels A and B). SEQ ID NO: 5 treatment blocked SBDP150 and SBDP145 formation to basal levels at 24 h post-injury (panel A, B, and E). In the vehicle control animals, SBDP145 levels continued to increase in the brain, becoming the predominant all-spectrin cleavage product at 48 h post-injury (see panels C and D). It is interesting to note that additional SBDPs of 120 (SBDP120) and 110 kDa (SBDP110), which were not present in the first 24 h post-injury, were generated by 48 h post-injury. SEQ ID NO: 5 treatment immediately after MCAO/reperfusion significantly reduced SBDP145 levels in the cortical and subcortical regions of the brain at 48 h post-injury (*P<0.05 vs. vehicle; n=6; 180 panel C, D, and E).

We have developed and used novel calpain inhibitors that exploit calpastatin's absolute specificity for calpain and a BBB-permeable drug delivery strategy and shows that postischemic inhibition of calpain significantly reduces infarct volume and improves neurological functional recovery after focal cerebral ischemia. In some embodiments, without limitation, a novel calpain inhibitor SEQ ID NO: 5 is comprised of a signal sequence-derived membrane translocation peptide motif identified through amino acids 23-36 of SEQ ID NO: 5 (VALLP AVLLA LLAP), conjugated to the C-terminus of human calpastatin subdomain B. SEQ ID NO: 5 is a potent, water-soluble, and specific inhibitor of calpain that is non-toxic to cultured cells.

Investigation of the pathobiology of cerebral ischemia indicates that the initial ischemic insult induces massive release of glutamate from damaged synapses which leads to activation of glutamate receptor-associated and voltage-dependent calcium channels. Such activation induces influx of calciumions into the neuron and release of calcium ions from intracellular stores. Loss of intracellular calcium homeostasis contributes to cell death by activating various enzymes, including proteases, kinases, phosphatases, and phospholipases. Integral to the mechanism of calcium-mediated brain injury is the pathologic activation of calpains. Under normal physiological conditions, calpain exists at very low activity in cells and is proposed to participate in the turnover of cytoskeletal proteins and the regulation of kinases, transcription factors, and receptors. However, pathologic calpain activation results in proteolytic destruction of many cellular proteins including receptor proteins, calmodulin binding proteins, signal transduction enzymes, transcription factors, and cytoskeletal proteins. Furthermore, uncontrolled calpain activity prevents increased expression of several key proteins, including growth-associated protein-43 (GAP-43), synaptophysin, and collapsin receptor mediator proteins (CRMPs), that play a major role in regeneration and neuroplasticity after ischemic and traumatic brain injury. Thus, calpains can contribute to the pathogenesis of ischemic brain injury via multiple molecular and cellular pathways. Thus, selective inhibition of calpains may lead to both cerebroprotective effects and an enhancement of neuronal plasticity/repair mechanisms.

We assessed functional outcome as an endpoint of our evaluation by the method of Bederson et al. Treatment with SEQ ID NO: 5 immediately after 2-h MCAO reduced neurological deficits by 24% and 44% on day 4 and day 7, respectively, compared to vehicle-treated stroke controls. Infarct volume was a secondary outcome and was measured at day 7 after stroke. The extent of cerebral infarction was reduced by 35% in the SEQ ID NO: 5-treated animals compared to vehicle-treated animals Due to the predictable location of areas of infarction and consistent production of neurological deficits in the MCAO model used in this study, the effects of SEQ ID NO: 5 on neurological outcome and size of infarction produced by focal cerebral ischemia could be reliably studied. It must be noted, however, that, infarction volumes could correlate poorly with functional outcome because small lesions in cortical locations can produce major functional deficits. Conversely, large lesions in relatively silent areas cause little detectable function loss. Reduction of neurological deficits after stroke has been attributed to synaptic and functional reorganization in the cerebral cortex and in subcortical structures after ischemic injuries. Since pathologic calpain activity can result in disruption of axonal transport and structural collapse as well as a net decrease in the level of proteins involved in the neuronal plasticity that occurs after brain injury, our data indicate that SEQ ID NO: 5 may effectively treat an array of calpain-mediated physiological changes associated with stroke to improve functional outcome.

The most well-studied calpain target is αII-spectrin, a 280-kDa neuronal protein that localizes to axons and functions in cortical cytoskeleton matrix support. αII-spectrin is proteolyzed by calpain to generate 150- and 145-kDa spectrin breakdown products (SBDP150 and SBDP145) or by caspase-3 to generate 150- and 120-kDa fragments (SBDP150i and SBDP120) following ischemic and traumatic brain injury. Calpain-generated SBDP145 is a signature biomarker for neuronal necrotic/oncotic cell death after ischemic and traumatic brain injury while caspase-3-generated SBDP120 is a signature biomarker for neuronal apoptosis. Recently, the clinical significance of calpain and caspase-3 specific SBDPs as biomarkers for acute brain injury was demonstrated in humans. Our data confirm that necrotic/oncotic and apoptotic cell death mechanisms overlap but appear to be activated at distinct time patterns after MCAO. As shown in FIGS. 4A and B, the extent of SBDP145 formation was similar in both cortical and subcortical regions of the ischemic hemisphere at 24 h post-injury. Interestingly, the SBDP145 levels increased about 3- and 2-fold in the cortex and subcortex, respectively, by 48 h after MCAO, suggesting continued calpain-mediated proteolysis of all-spectrin in the ischemic hemisphere probably due to a new surge in intracellular $Ca^{2+}$ ($[Ca^{2+}]i$) levels in this region of the brain that resulted in an additional increase in calpain activation between 24 and 48 h following the initial ischemic injury. While acute postischemic administration of SEQ ID NO: 5 completely blocked SBDP145 accumulation at 24 h post-injury, the treatment significantly reduced SBDP145 levels in the cortex and the subcortex at 48 h. In addition to its use in assessing neuronal structural degradation and evaluating possible mechanisms involved in the evolving brain damage after stroke, we have demonstrated the potential utility of SBDP145 biomarker as an adjunct in guiding therapeutic decision making during the development of calpain-target-based neuroprotective strategies.

To date, preclinical studies reported on anti-calpain treatment strategies for stroke have used inhibitor designs based on diortripeptide and peptidomimetic address labels modified with a chemical warhead. Even though these small molecule synthetic inhibitors are effective in inhibiting calpain, they do, to varying degrees, react with other proteases implicated in the pathophysiology of stroke. It could be argued that single-drug therapy with a broad-spectrum inhibitor that blocks several proteases involved in the progression of ischemic brain injury would be more effective than treatment with a highly selective inhibitor that targets one particular protease. However, the lack of specificity of a protease inhibitor often raises other issues related to tissue toxicity. Furthermore, the onset, duration, and extent (amount) of abnormal protease activity generated after the initial ischemic event are likely to be different for each protease target. Our findings indicate that a protease-targets-based combination therapy aimed at selective inhibition of unique steps of protease-mediated brain injury would result in synergistic brain tissue protection and improvement of functional outcome after stroke.

Example 3

We used SEQ ID NO: 5 to investigate the role of calpain in neurovascular dysfunction after stroke.

Two-hour middle cerebral artery occlusion (MCAO) was used to induce ischemic stroke in Male Wistar rats. SEQ ID NO: 5 was given intravenously to rats immediately after reperfusion following 2 h of MCAO, while control animals had infusion of vehicle solution (n=6-9). Animals to be studied for neurological score and infarct volume survived 7 days, and neurological testing (mNSS and corner turn) were performed at 1, 4, and 7 days after MCAO. In another set of experiments, the animals were sacrificed at 48 h, and histology was performed for BBB integrity (albumin and fibrin leakage from the cerebral microvasculature into brain parenchyma). Phosphorylation of endothelial nitric oxide synthase (eNOS) was analyzed by Western blotting with specific antibodies raised against synthetic phosphorylated peptides representing known eNOS phosphorylation sites.

Results:

Postischemic administration of SEQ ID NO: 5 reduced infarct volume and neurological deficits by 35% and 44%, respectively, compared to untreated animals (p<0.05 for each). BBB integrity as assessed by albumin and fibrin extravasation showed significant improvement after SEQ ID NO: 5 treatment compared to controls (p<0.05) at 48 h. Endothelial nitric oxide synthase (eNOS) threonine-495 phosphorylation which was found to be highly upregulated (~3-fold) in the brain after stroke was significantly reduced by treatment with SEQ ID NO: 5. Thus, we discovered unexpectedly that treatment of transient cerebral ischemia with a specific calpastatin-based inhibitor of calpain has neuroprotective and functional recovery associated with regulation of eNOS and vasoprotection, as can be seen from its beneficial effects on BBB integrity.

Figure 5:
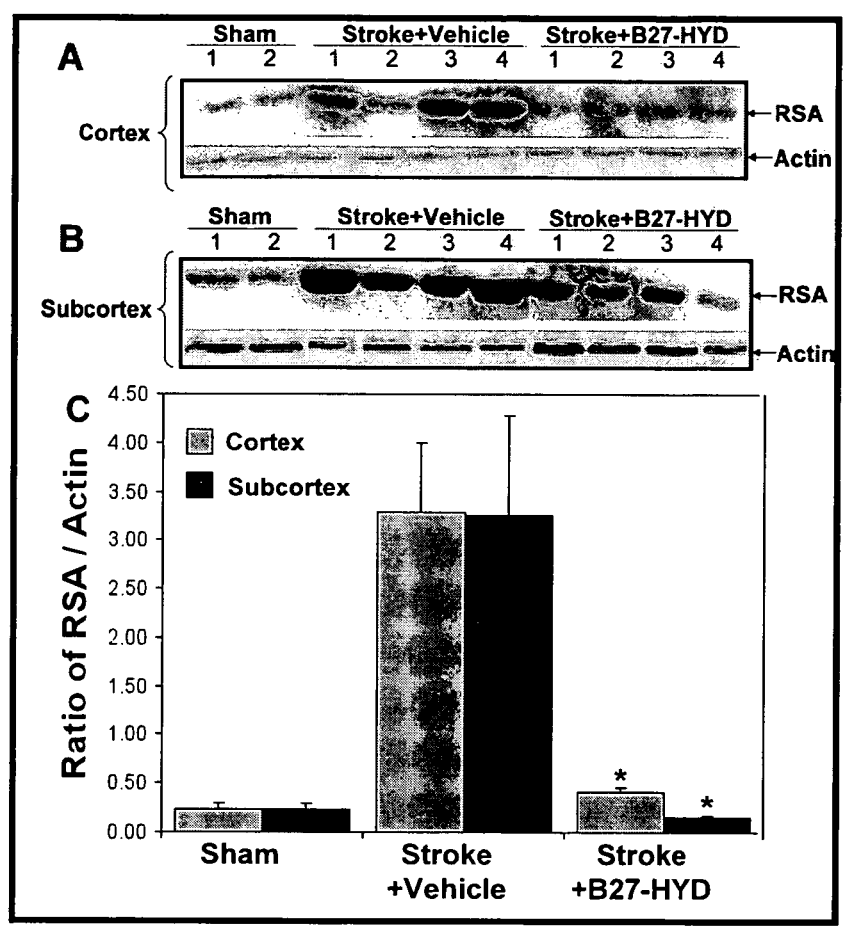
FIG. 5 shows data indicating that SEQ ID NO: 5 reduces rat serum albumin (RSA) leakage into the ischemic brain parenchyma.

FIG. 5 shows data indicating that SEQ ID NO: 5 reduces rat serum albumin (RSA) leakage into the ischemic brain parenchyma. Shown are representative immunoblots of RSA levels in the ipsilateral cortical (A) and subcortical (B) regions of sham-operated, ischemic vehicle-treated, and ischemic. C, Densitometric analysis of RSA levels in ipsilateral cortex and subcortex (*p<0.05 vs vehicle; n=6) at 24 h following MCAO.

Figure 6:
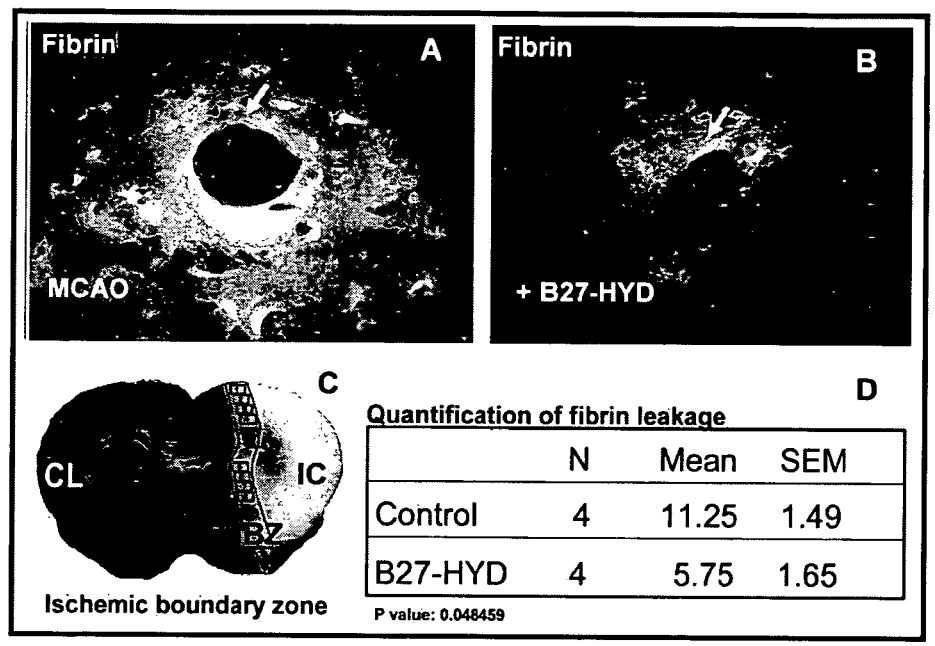
FIG. 6 shows data indicating that SEQ ID NO: 5 treatment decreases fibrin deposition outside the cerebral microvasculature.

FIG. 6 shows data indicating that SEQ ID NO: 5 treatment decreases fibrin deposition outside the cerebral microvasculature. Representative fluorescent micrographs of fibrin deposition outside the cerebral microvasculature of untreated (MCAO, panel A) and treated (+SEQ ID NO: 5, panel B) rats subjected to 2 hour MCA occlusion with reperfusion and 48 hour survival are shown. A schematic representation of a coronal brain section showing eight fields selected from the ischemic boundary zone (IBZ) for quantitative measurements of immunochemical staining for fibrin in the cortex and striatum is shown (panel C). The quantitative data confirms that SEQ ID NO: 5 treatment of stroke significantly decreases BBB leakage compared to control MCAO rats (panel D).

Figure 7:
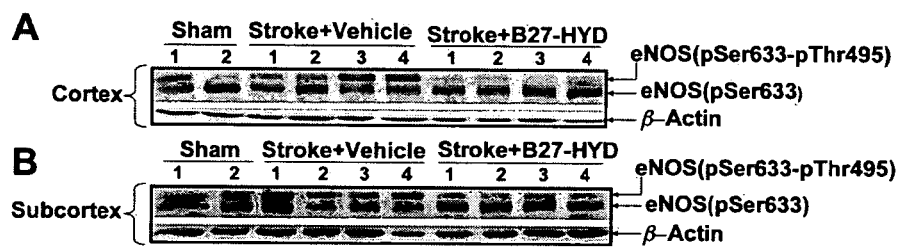
FIG. 7 shows data indicating that SEQ ID NO: 5 modulates eNOS phosphorylation state.
Figure 7:
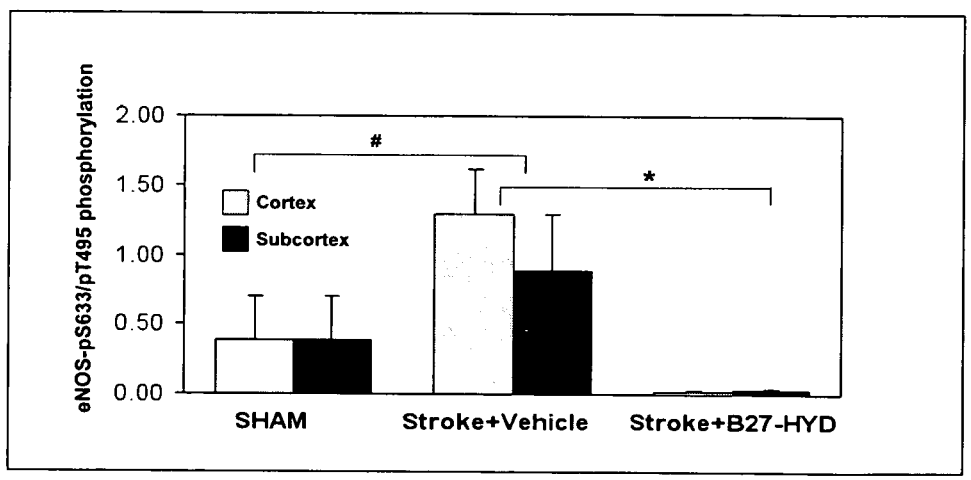

FIG. 7 shows data indicating that SEQ ID NO: 5 modulates eNOS phosphorylation state: A-B: Both upper and lower bands are phosphorylated at eNOS-Ser633. C: Graphical representation of the ratio of upper:lower phospho-eNOS protein band intensities (n=6 rats/experimental group).

Figure 8:
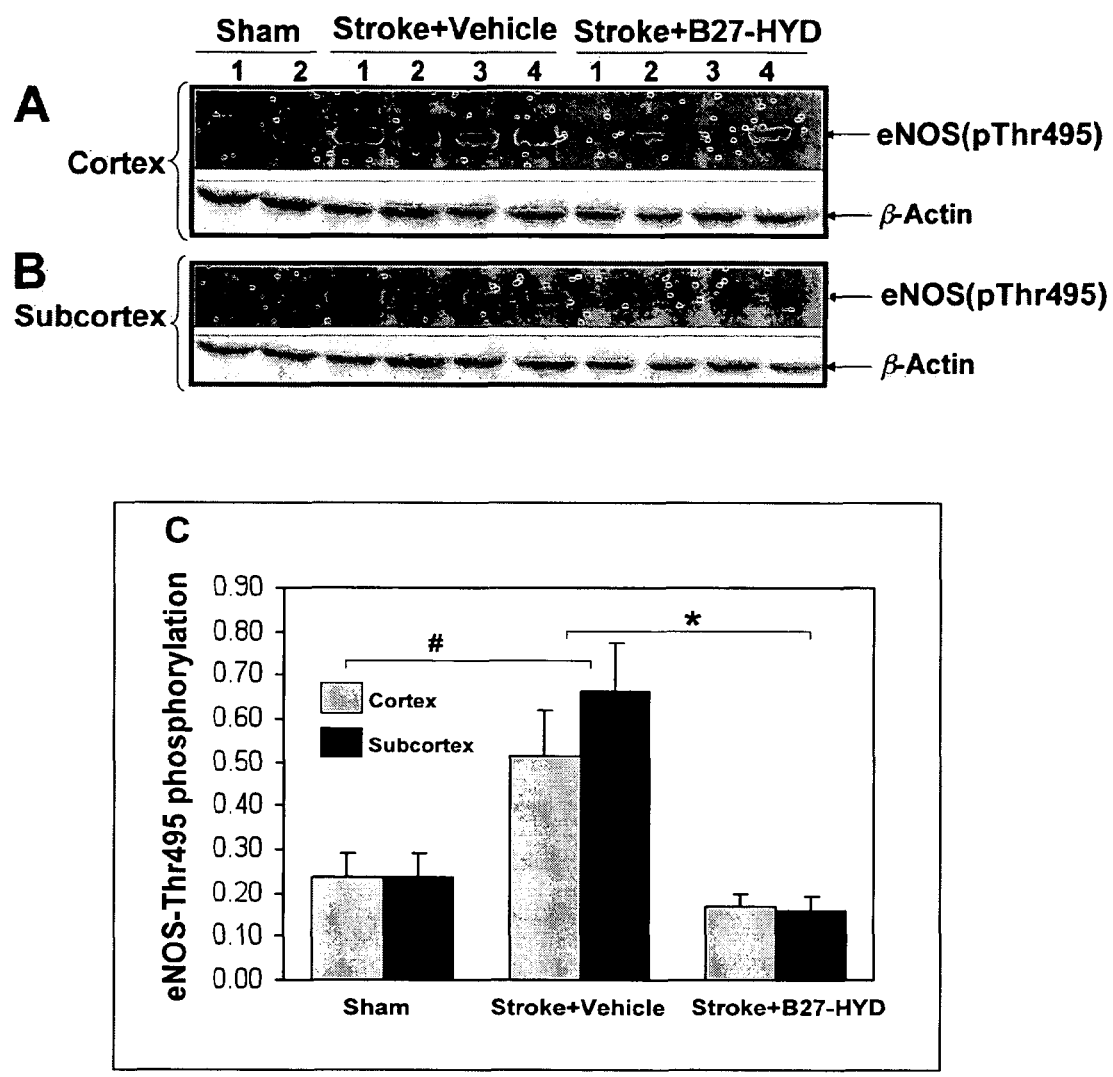
FIG. 8 shows data indicating that post-injury treatment with SEQ ID NO: 5 induces eNOS-Thr495 dephosphorylation

FIG. 8 shows data indicating that post-injury treatment with SEQ ID NO: 5 induces eNOS-Thr495 dephosphorylation Stroke is a leading cause of death and long-term disability without any definitive treatments that have been demonstrated to improve functional outcomes. Accumulated evidence implicates calpains in the pathogenesis of ischemic brain injury via multiple molecular and cellular pathways. In vivo inhibition of calpain using cysteine protease inhibitors (e.g. peptide aldehydes, alpha-keto esters and amides) diminishes the extent of neuronal damage following ischemia; however, the relative non-specificity of these cysteine protease inhibitors precludes a definitive role for calpain participation. Traditionally, calpain-mediated postischemic neurological dysfunction has been attributed mainly to the enzyme's destructive proteolysis of cytoskeletal proteins leading to necrotic and/or apoptotic cell death. However, calpains can also participate in neurovascular cell signaling events via proteolytic activation of kinases and phosphatases. Nitric oxide (NO) serves as an endogenous vasodilator, platelet inhibitor, antioxidant, and regulator of vascular endothelium by sustaining its anti-coagulant and anti-thrombogenic properties. Mice lacking the constitutively expressed form of endothelial nitric oxide synthase (eNOS) exhibit larger cerebral infarctions and upregulation of eNOS with L-arginine and statins protects against stroke. More importantly, eNOS activity is regulated through multiple and coordinated phosphorylation events at various phosphorylation sites mediated by multiple kinases. The literature to date indicates that six specific sites of phosphorylation have been identified in human eNOS at Tyr81, Ser114, Thr495, Ser615, Ser633, and Ser1177. Depending on the site, phosphorylation of eNOS could either activate the enzyme or attenuate enzyme activity. Phosphorylation of eNOS-Ser633 increases eNOS activity and appears particularly important for maintenance of NO synthesis after initial activation by Ca2+ flux and eNOS-Ser1177 phosphorylation. In contrast, phosphorylation of eNOS-Thr495 in the Ca2+/calmodulin (CaM) binding domain is inhibitory. In this study, we benefited from the absolute specificity of calpastatin to inhibit calpain pharmacologically and to investigate the mechanism of calpain in neurovascular dysfunction after stroke.

Our findings substantiate the involvement of calpain in postischemic neurological and cerebrovascular dysfunction and show a protective mechanism of SEQ ID NO: 5. The protective mechanism is, in part, due to preservation of cerebral endothelial function. An interesting finding is that calpain is involved in regulation of endothelial nitric oxide synthase, a key enzyme involved in neurovascular function, through phosphorylation events. SEQ ID NO: 5 as a novel BBB-permeant specific inhibitor of calpain provides a novel approach for the treatment of stroke, as well as for investigating the mechanism(s) of calpain-mediated neurodegenerative disorders. Embodiments of the invention may expand the therapeutic window for ischemic stroke and could be applied to a large portion of the many patients who suffer stroke each year worldwide.

Thus, without limitation and without disclaimer of subject matter, some embodiments comprise novel compositions and methods to prevent, control, or alleviate mammalian injury, including without limitation, brain damage, through the selective application of novel calpain inhibitors. In accordance with some embodiments, without limitation, one may inhibit such trauma through the administration of one or more such inhibitors for a finite interval of time, thereby limiting the development of such damage.

In accordance with some embodiments, there is a high likelihood that the duration of drug therapy would be relatively brief and with a high probability of success. Prophylactic administration of efficacious amounts of the calpain inhibitors of some embodiments may greatly reduce the incidence of damage associated with many forms of neural trauma.

In accordance with some embodiments, a route of administration of the calpain inhibitors of some embodiments in humans is by oral administration. However, any appropriate routes of administering such inhibitors known to those of ordinary skill in the art also comprise embodiments of the invention.

The calpain inhibitor(s) of some embodiments would be administered and dosed in accordance with good medical practice, taking into account the clinical condition of the individual patient, the site and method of administration, scheduling of administration, patient age, sex, body weight and other factors known to medical practitioners. The "pharmaceutically effective amount" for purposes herein is thus determined by such considerations as are known in the art. The amount must be effective to achieve improvement, including but not limited to, decreased damage or injury, or improvement or elimination of symptoms and other indicators as are selected as appropriate measures by those skilled in the art.

In accordance with some embodiments, such calpain inhibitor(s) can be administered in various ways. It can be administered alone or as an active ingredient in combination with pharmaceutically acceptable carriers, diluents, adjuvants and vehicles. The inhibitor(s) can be administered orally, subcutaneously or parenterally including intravenous, intraarterial, intramuscular, intraperitoneal, and intranasal administration as well as intrathecal and infusion techniques, or by local administration or direct inoculation to the site of disease or pathological condition. Implants of the compounds are also useful. The patient being treated is a warm-blooded animal and, in particular, mammals including humans. The pharmaceutically acceptable carriers, diluents, adjuvants and vehicles as well as implant carriers generally refer to inert, non-toxic solid or liquid fillers, diluents or encapsulating material not reacting with the active ingredients of the invention.

Since the use of such the calpain inhibitors in accordance with some embodiments specifically targets the evolution and expression of associated pathologies, it is expected that the timing and duration of treatment in humans will approximate those established for animal models. Similarly, the doses established for achieving desired effects using such compounds in animal models, or for other clinical applications, would be expected to be applicable in this context as well. SEQ ID NO: 5 is water soluble and dissolved in PBS. We have infused SEQ ID NO: 5 at a concentration of 50 micromolar solution via femoral vein for 4 hours after reperfusion of the middle cerebral artery for a total dose of 3 mg/kg. This dose was effective at improving neurological recovery in this stroke model. When studying another cysteine protease inhibitor (which blocks cathepsins B and L) in this stroke model in a similar fashion, we found that 4 hour infusion of concentrations of 10, 50, and 250 micromolar were equally effective at reducing neurological impairment, whereas 2 micromolar solutions was not effective. It is noted that humans are treated generally longer than the experimental animals exemplified herein which treatment has a length proportional to the length of the disease process and drug effectiveness. The doses may be single doses or multiple doses over periods of time. The treatment generally has a length proportional to the length of the disease process and drug effectiveness and the patient species being treated. Without limiting or disclaiming any embodiments, a therapeutically effective amount of the compound described herein preferably ranges from about 0.01 milligrams per kilogram of body weight per day (mg/kg/day) to about 100 mg/kg/day. Preferred amounts are expected to vary from about 0.5 to about 30 mg/kg/day.

When administering the calpain inhibitor(s) of some embodiments parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

When necessary, proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for such calpain inhibitor(s) compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the calpain inhibitor(s).

Sterile injectable solutions can be prepared by incorporating the inhibitor(s) utilized in practicing the present invention in the required amount of the appropriate solvent with various of the other ingredients, as desired.

A pharmacological formulation of some embodiments may be administered to the patient in an injectable formulation containing any compatible carrier, such as various vehicle, adjuvants, additives, and diluents; or the inhibitor(s) utilized in some embodiments may be administered parenterally to the patient in the form of slow-release subcutaneous implants or targeted delivery systems such as monoclonal antibodies, vectored delivery, iontophoretic, polymer matrices, liposomes, and microspheres. Many other such implants, delivery systems, and modules are well known to those skilled in the art.

In some embodiments, without limitation, the calpain inhibitor(s) of some embodiments may be administered initially by intravenous injection to bring blood levels to a suitable level. The patient's levels are then maintained by an oral dosage form, although other forms of administration, dependent upon the patient's condition and as indicated above, can be used. The quantity to be administered and timing of administration may vary for the patient being treated.

This application may reference various publications by author, citation, and/or by patent number, including without limitation, articles, presentations, and United States patents. The disclosures of each of these references in their entireties are hereby incorporated by reference into this application.

While the present invention has been particularly shown and described with reference to the foregoing preferred and alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

Disclosed Nucleic Acid And Peptide Sequences

```
SEQ ID NO: 1:
acc caa tgg cta cta cct acc taa gag gaa ttg ggt aaa aga gaa gtc aca att cct cca aaa tat agg gaa cta ttg gct SEQ ID NO: 2:
Asp Pro Met Ser Ser Thr Tyr Ile Glu Glu Leu Gly Lys Arg Glu Val Thr Ile Pro Pro Lys Tyr Arg Glu Leu Leu Ala SEQ ID NO: 3:
Asp Pro Met Ser Ser Thr Tyr Ile Glu Glu Leu Gly Lys Arg Glu Val Thr Ile Pro Pro Lys Tyr Val Ala Leu Leu Pro SEQ ID NO: 4:
Ala Val Leu Leu Ala Leu Leu Ala Pro SEQ ID NO: 5:
Asp Pro Met Ser Ser Thr Tyr Ile Glu Glu Leu Gly Lys Arg Glu Val Thr Ile Pro Pro Lys Tyr Val Ala Leu Leu Pro Ala Val Leu Leu Ala Leu Leu Ala Pro SEQ ID NO: 6:
Asp Pro Met Ser Ser Thr Tyr Ile Glu Glu Leu Gly Lys Arg Glu Val Thr Nva Pro Pro Lys Tyr Orn Glu Leu Leu Ala
```

-continued

SEQ ID NO: 7:
Asp Pro Met Ser Ser Thr Tyr Ile Glu Glu Leu Gly

Lys Arg Glu Val Thr Nva Pro Pro Lys Tyr Arg Glu

Leu Leu Ala

SEQ ID NO: 8:
Asp Pro Met Ser Ser Thr Tyr Ile Glu Glu Leu Gly

Lys Arg Glu Val Thr Ile Pro Pro Lys Tyr Orn Glu

Leu Leu Ala

SEQ ID NO: 9:
Asp Pro Met Ser Ser Thr Tyr Ile Glu Glu Leu Gly

Lys Arg Glu Val Thr Nva Pro Pro Lys Tyr Val Ala

Leu Leu Pro

SEQ ID NO: 10:
Asp Pro Met Ser Ser Thr Tyr Ile Glu Glu Leu Gly

Lys Arg Glu Val Thr Nva Pro Pro Lys Tyr Val Ala

Leu Leu Pro Ala Val Leu Leu Ala Leu Leu Ala Pro

SEQ ID NO: 11:
gcc gcg gta gcg ctg ctc ccg gcg gtc ctg ctg gcc ttg ctg gcg ccc

SEQ ID NO: 12:
Ala Ala Val Ala Leu Leu Pro Ala Val Leu Leu Ala

Leu Leu Ala Pro

SEQ ID NO: 13:
Asp Pro Met Ser Ser Thr Tyr Ile Glu Glu βAla Gly

Lys Arg Glu Val Thr Ile Pro Pro Lys Tyr Val Ala

Leu Leu Pro Ala Val Leu Leu Ala Leu Leu Ala Pro

---

What is claimed is:

1. A synthetic peptide comprising SEQ ID NO: 5.

2. A composition comprising:
   the peptide of claim 1; and
   an additive selected from the group consisting of a hydrophobic blood-brain-barrier or a membrane-permeant amino acid sequence linked by a polyethylene glycol linker to the N-terminus of said peptide, SEQ ID NO. 11, SEQ ID NO. 12, a nonaqueous vehicle, a solvent, a diluent, adjuvant, a chelating agent, a stability enhancing additive, antimicrobial preservatives, antioxidants, buffers, an antibacterial or an antifungal agents, parabens, chlorobutanol, phenol, sorbic acid, an isotonic agent, a sugar, sodium chloride, a prolonged absorption agent, aluminum monostearate, a gelatin and combinations thereof.

3. A method of inhibiting neuronal damage in a subject following an ischemic event, comprising the steps of:
   providing the composition of claim 2, and
   administering a pharmaceutically effective amount of said composition to the subject.

4. A drug for inhibiting neural damage in a subject following an ischemic event, the drug comprising:
   the peptide of claim 1; and
   a pharmaceutically acceptable excipient or other additive selected from the group consisting of a hydrophobic blood-brain-barrier or a membrane-permeant amino acid sequence linked by a polyethylene glycol linker to the N-terminus of said peptide, SEQ ID NO. 11, SEQ ID NO. 12, a nonaqueous vehicle, a solvent, a diluent, adjuvant, a chelating agent, a stability enhancing additive, antimicrobial preservatives, antioxidants, buffers, an antibacterial or an antifungal agents, parabens, chlorobutanol, phenol, sorbic acid, an isotonic agent, a sugar, sodium chloride, a prolonged absorption agent, aluminum monostearate, a gelatin and combinations thereof.

5. A composition comprising:
   one or more peptides of SEQ ID NOS: 3, 5, 6, 7, 8, 9, and 10.; and
   a pharmaceutically acceptable excipient or other additive selected from the group consisting of a hydrophobic blood-brain-barrier or a membrane-permeant amino acid sequence linked by a polyethylene glycol linker to the N-terminus of said peptide, SEQ ID NO. 11, SEQ ID NO. 12, a nonaqueous vehicle, a solvent, a diluent, a chelating agent, a stability enhancing additive, antimicrobial preservatives, antioxidants, buffers, an antibacterial or an antifungal agents, parabens, chlorobutanol, phenol, sorbic acid, an isotonic agent, a sugar, sodium chloride, a prolonged absorption agent, aluminum monostearate, a gelatin and combinations thereof.

6. A method of inhibiting neuronal damage in a subject following an ischemic event, comprising the steps of:
   providing the composition of claim 5, and
   administering a pharmaceutically effective amount of said composition to the subject.

7. A drug for inhibiting neural damage in a subject following an ischemic event, the drug comprising:
   one or more peptide of SEQ ID NOS: 3, 5, 6, 7, 8, 9, or 10; and
   a pharmaceutically acceptable excipient or other additive selected from the group consisting of a hydrophobic blood-brain-barrier or a membrane-permeant amino acid sequence linked by a polyethylene glycol linker to the N-terminus of said peptide, SEQ ID NO. 11, SEQ ID NO. 12, a nonaqueous vehicle, a solvent, a diluent, a chelating agent, a stability enhancing additive, antimicrobial preservatives, antioxidants, buffers, an antibacterial or an antifungal agents, parabens, chlorobutanol, phenol, sorbic acid, an isotonic agent, a sugar, sodium chloride, a prolonged absorption agent, aluminum monostearate, a gelatin and combinations thereof.

8. A synthetic peptide comprising SEQ ID NO: 2 or SEQ ID NO: 5 wherein the peptidic bond(s) of one or more of the following amino acid pairs in the sequence is replaced with a non-peptidic reduced amide bond: Ser4-Ser5, Tyr6-Ile7, Lys13-Arg14, Glu15-Val16, Lys21-Tyr22, Tyr22-Arg23.

9. A method of inhibiting neuronal damage in a subject following an ischemic event, comprising the steps of:
providing a composition comprised of the synthetic peptide of claim 8, and administering a pharmaceutically effective amount of said composition to the subject.

10. A drug for inhibiting neural damage in a subject following an ischemic event, the drug comprising:
the synthetic peptide of claim 8; and
a pharmaceutically acceptable excipient or other additive selected from the group consisting of a hydrophobic blood-brain-barrier or a membrane-permeant amino acid sequence linked by a polyethylene glycol linker to the N-terminus of said peptide, SEQ ID NO. 11, SEQ ID NO. 12, a nonaqueous vehicle, a solvent, a diluent, a chelating agent, a stability enhancing additive, antimicrobial preservatives, antioxidants, buffers, an antibacterial or an antifungal agents, parabens, chlorobutanol, phenol, sorbic acid, an isotonic agent, a sugar, sodium chloride, a prolonged absorption agent, aluminum monostearate, a gelatin and combinations thereof.

11. A synthetic peptide comprising SEQ ID NO: 2, wherein there is side-chain cyclization between Lys21 and Glu24.

12. A method of inhibiting neuronal damage in a subject following an ischemic event, comprising the steps of:
providing a composition comprised of the synthetic peptide of claim 11, and
administering a pharmaceutically effective amount of said composition to the mammal.

13. A drug for inhibiting neural damage in a subject following an ischemic event, the drug comprising:
the synthetic peptide of claim 11; and
a pharmaceutically acceptable excipient or other additive selected from the group consisting of a hydrophobic blood-brain-barrier or a membrane-permeant amino acid sequence linked by a polyethylene glycol linker to the N-terminus of said peptide, SEQ ID NO. 11, SEQ ID NO. 12, a nonaqueous vehicle, a solvent, a diluent, a chelating agent, a stability enhancing additive, antimicrobial preservatives, antioxidants, buffers, an antibacterial or an antifungal agents, parabens, chlorobutanol, phenol, sorbic acid, an isotonic agent, a sugar, sodium chloride, a prolonged absorption agent, aluminum monostearate, a gelatin and combinations thereof.

* * * * *

SEQUENCE LISTING

```
<160> NUMBER OF SEQ IDS NOS: 13

<210> SEQ ID NO 1
<211> LENGTH: 81
<212> TYPE: DNA
<213> ORGANISM: Homo sapiens

<400> SEQUENCE: 1
acccaatggc tactacctac ctaagaggaa ttgggtaaaa gagaagtcac aattcctcca    60
aaatataggg aactattggc t                                              81

<210> SEQ ID NO 2
<211> LENGTH: 27
<212> TYPE: PRT
<213> ORGANISM: Homo sapiens

<400> SEQUENCE: 2

Asp Pro Met Ser Ser Thr Thr Ile Glu Glu Leu Gly Lys Arg Glu Val
1               5                   10                  15

Thr Ile Pro Pro Lys Tyr Arg Glu Leu Leu Ala
            20                  25

<210> SEQ ID NO 3
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Pro Met Ser Ser Thr Thr Ile Glu Glu Leu Gly Lys Arg Glu Val
1               5                   10                  15

Thr Ile Pro Pro Lys Tyr Val Ala Leu Leu Pro
            20                  25

<210> SEQ ID NO 4
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 4

Ala Val Leu Leu Ala Leu Leu Ala Pro
1               5

<210> SEQ ID NO 5
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Pro Met Ser Ser Thr Thr Ile Glu Glu Leu Gly Lys Arg Glu Val
1               5                   10                  15

Thr Ile Pro Pro Lys Tyr Val Ala Leu Leu Pro Ala Val Leu Leu Ala
            20                  25                  30

Leu Leu Ala Pro
        35

<210> SEQ ID NO 6
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Nva
<220> FEATURE:
<221> NAME/KEY: MOD_RES
<222> LOCATION: (23)..(23)
<223> OTHER INFORMATION: Orn

<400> SEQUENCE: 6

Asp Pro Met Ser Ser Thr Thr Ile Glu Glu Leu Gly Lys Arg Glu Val
1               5                   10                  15

Thr Val Pro Pro Lys Tyr Xaa Glu Leu Leu Ala
            20                  25

<210> SEQ ID NO 7
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Nva

<400> SEQUENCE: 7

Asp Pro Met Ser Ser Thr Thr Ile Glu Glu Leu Gly Lys Arg Glu Val
1               5                   10                  15

Thr Val Pro Pro Lys Tyr Arg Glu Leu Leu Ala
            20                  25

<210> SEQ ID NO 8
<211> LENGTH: 27
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (23)..(23)
<223> OTHER INFORMATION: Orn

<400> SEQUENCE: 8

Asp Pro Met Ser Ser Thr Thr Ile Glu Glu Leu Gly Lys Arg Glu Val
1               5                   10                  15

Thr Ile Pro Pro Lys Tyr Xaa Glu Leu Leu Ala
            20                  25

<210> SEQ ID NO 9
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Nva

<400> SEQUENCE: 9

Asp Pro Met Ser Ser Thr Thr Ile Glu Glu Leu Gly Lys Arg Glu Val
1               5                   10                  15

Thr Val Pro Pro Lys Tyr Val Ala Leu Leu Pro
            20                  25

<210> SEQ ID NO 10
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (18)..(18)
<223> OTHER INFORMATION: Nva

<400> SEQUENCE: 10

Asp Pro Met Ser Ser Thr Thr Ile Glu Glu Leu Gly Lys Arg Glu Val
1               5                   10                  15

Thr Val Pro Pro Lys Tyr Val Ala Leu Leu Pro Ala Val Leu Leu Ala
            20                  25                  30

Leu Leu Ala Pro
        35

<210> SEQ ID NO 11
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gccgcggtag cgctgctccc ggcggtcctg ctggccttgc tggcgccc                 48

<210> SEQ ID NO 12
<211> LENGTH: 25
<212> TYPE: PRT
<213> ORGANISM: Artificial Sequence
<220> FEATURE:
<223> OTHER INFORMATION: Description of Artificial Sequence: Synthetic
```

```
                               peptide

<400> SEQUENCE: 12

Ala Ala Val Ala Leu Leu Pro Ala Val Leu Leu Ala Leu Leu Ala Pro
1               5                   10                  15

Ala Val Leu Leu Ala Leu Leu Ala Pro
            20                  25

<210> SEQ ID NO 13
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (11)..(11)
<223> OTHER INFORMATION: Beta-Ala

<400> SEQUENCE: 13

Asp Pro Met Ser Ser Thr Thr Ile Glu Glu Ala Gly Lys Arg Glu Val
1               5                   10                  15

Thr Ile Pro Pro Lys Tyr Val Ala Leu Leu Pro Ala Val Leu Leu Ala
            20                  25                  30

Leu Leu Ala Pro
            35
```